(12) United States Patent
Chen et al.

(10) Patent No.: US 12,702,367 B2
(45) Date of Patent: Aug. 11, 2026

(54) HEIGHT COMPENSATION SYSTEM FOR PATIENT TABLE

(71) Applicant: Siemens Shanghai Medical Equipment Ltd., Shanghai (CN)

(72) Inventors: Jia Jian Chen, Shanghai (CN); Ping Zhu, Shanghai (CN)

(73) Assignee: Siemens Shanghai Medical Equipment Ltd., Shanghai (CN)

(*) Notice: Subject to any disclaimer, the term of this patent is extended or adjusted under 35 U.S.C. 154(b) by 301 days.

(21) Appl. No.: 18/706,451

(22) PCT Filed: Nov. 3, 2021

(86) PCT No.: PCT/CN2021/128448

§ 371 (c)(1),
(2) Date: May 1, 2024

(87) PCT Pub. No.: WO2023/077307

PCT Pub. Date: May 11, 2023

(65) Prior Publication Data

US 2026/0157710 A1 Jun. 11, 2026

(51) Int. Cl.
*A61B 6/04* (2006.01)
*A61B 5/00* (2006.01)
(Continued)

(52) U.S. Cl.
CPC ............ *A61B 6/0492* (2013.01); *A61B 5/704* (2013.01); *A61B 5/706* (2013.01); *A61B 6/0407* (2013.01);
(Continued)

(58) Field of Classification Search
CPC ....... A61B 6/0407; A61B 6/04; A61B 6/0492; A61B 5/704; A61B 5/706; A61B 6/0487; A61B 6/102; A61B 5/055; A61B 6/03
(Continued)

(56) References Cited

U.S. PATENT DOCUMENTS 5,825,843 A * 10/1998 Kobayashi ............ A61B 6/102 378/209
8,191,190 B2 * 6/2012 Zapata ................ A61B 6/0487 5/601
(Continued)

FOREIGN PATENT DOCUMENTS

DE 102020200466 A1 * 7/2021 ............ A61B 5/055
JP 2009247391 A * 10/2009 .......... A61B 6/5276

OTHER PUBLICATIONS

Trans. DE-102020200466-A1 (Year: 2026).*
(Continued)

*Primary Examiner* — J. T. Newton
(74) *Attorney, Agent, or Firm* — Banner & Witcoff, Ltd.

(57) ABSTRACT

A height compensation system for a patient table, including: a light reflection block, which is disposed on a gantry side of a medical device, and is configured to reflect a received optical signal; a photoelectric detector, which is disposed on the patient table opposite to the light reflection block, and is configured to emit an optical signal outward and detect a reflected signal of the optical signal; and a controller, which is communicably connected to the photoelectric detector, and configured to control, when the photoelectric detector detects a reflected signal reflected by the light reflection block, the patient table to move upward in a vertical direction until the photoelectric detector does not detect the reflected signal reflected by the light reflection block.

8 Claims, 3 Drawing Sheets

(51) Int. Cl.
*A61B 5/055* (2006.01)
*A61B 6/03* (2006.01)
*A61B 6/10* (2006.01)

(52) U.S. Cl.
CPC ............ *A61B 6/0487* (2020.08); *A61B 6/102* (2013.01); *A61B 5/055* (2013.01); *A61B 6/03* (2013.01)

(58) Field of Classification Search
USPC ............................................. 378/209; 5/601
See application file for complete search history.

(56) References Cited

U.S. PATENT DOCUMENTS

2015/0289826 A1* 10/2015 Herold ................. A61B 6/0407 378/209
2018/0133508 A1* 5/2018 Pearce .................. A61B 6/583

OTHER PUBLICATIONS

Trans. JP-2009247391-A (Year: 2026).*
Apr. 7, 2022 (PCT) International Search Report—App. PCT/CN2021/128448.

* cited by examiner

HEIGHT COMPENSATION SYSTEM FOR PATIENT TABLE

TECHNICAL FIELD

The present disclosure relates to the medical field, and more specifically, to a height compensation system for a patient table.

BACKGROUND

In a medical device for examinations such as computed tomography (CT) or magnetic resonance imaging (MRI) examinations, a patient table for examination is generally supported by a scissors-like vertical structure outside a gantry of the medical device.

When a heavy patient (for example, a patient weighing more than 220 kg) lies on the patient table, the patient table may be deformed to some extent, causing a head end of the patient table to be lower and a foot end to be higher. Such a case may cause the head end of the patient table to be lower than the height of a plane of a bracket (that is, a reference height) that is in the gantry and that is configured to support the patient table, and the patient table cannot enter the gantry or has relatively large friction with the plane of the bracket when entering the gantry, resulting in a colliding horizontal movement of the patient table into the gantry and poor experience of the patient.

To resolve the foregoing problems, in the related art, a vertical height of a patient table is positioned by using a reflective photoelectric detector. When a heavy patient lies on the patient table, a height of the head end of the patient table is manually adjusted to a reference height, which is a cumbersome process.

In addition, when the heavy patient gets out of the patient table after the examination, the head end of the patient table originally deformed and lowered recovers. As a result, the height of the patient table is higher than the reference height. If a next patient is lighter, when the patient table conveys the patient into the gantry, the patient table moves suspended from the plane of the bracket in the gantry until the weight of the patient is heavy enough to press the patient table onto the plane of the bracket, which severely affects the smoothness and safety of a movement of the patient table and the comfort of the patient.

SUMMARY

In view of the status and deficiencies of the related art, an objective of the present disclosure is to provide a height compensation system for a patient table. When a heavy patient lies on a patient table, a height of the patient table is automatically adjusted upward to a reference height by detecting a signal change of a photoelectric sensor. A height change of a foot end of the patient table is detected by using a height sensor, to determine whether to automatically adjust the patient table downward. When the patient table needs to be adjusted downward, a height of the patient table is automatically adjusted downward to the reference height by detecting a signal change of the photoelectric detector, thereby automatically performing height compensation on the patient table, reducing mechanical interference and deformations during the use of the patient table and prolonging the service life of an examination apparatus, while enhancing the smoothness and safety of a horizontal movement of the patient table and improving the comfort of the patient.

According to an aspect of embodiments of the present disclosure, a height compensation system for a patient table is provided, to control a relative position between a patient table and a gantry of a medical device. The height compensation system for a patient table includes: a light reflection block, disposed on a gantry side of the medical device or a patient table side, and configured to reflect a received optical signal; a photoelectric detector, disposed on the gantry side or the patient table side opposite to the light reflection block, and configured to emit an optical signal outward and detect a reflected signal of the optical signal; and a controller, communicably connected to the photoelectric detector, and configured to control, when the photoelectric detector detects a reflected signal reflected by the light reflection block, the patient table to move upward in a vertical direction, until the photoelectric detector does not detect the reflected signal reflected by the light reflection block.

When the photoelectric detector detects the reflected signal, it is determined that a heavy patient uses the patient table, and the patient table is controlled to move upward in the vertical direction until the photoelectric detector no longer detects the reflected signal, so as to automatically adjust a height of the deformed patient table to a reference height, thereby avoiding mechanical interference when the patient table enters the gantry of the medical device, ensuring the safety of a horizontal movement of the patient table, and improving the comfort of the patient.

In the height compensation system for a patient table according to the embodiments of the present disclosure, the light reflection block is disposed on the gantry side of the medical device, and the photoelectric detector is disposed on the patient table side opposite to the light reflection block.

A specific setting form of positions of the light reflection block and the photoelectric detector is provided.

In the height compensation system for a patient table according to the embodiments of the present disclosure, the light reflection block is disposed on the patient table side, and the photoelectric detector is disposed on the gantry side of the medical device.

Another specific setting form of positions of the light reflection block and the photoelectric detector is provided.

The height compensation system for a patient table according to the embodiments of the present disclosure further includes: a height sensor, configured to detect height compensation information of a vertical height of the patient table from a base of the medical device relative to a reference height, where the controller is communicably connected to the height sensor and is further configured to determine, according to the height compensation information when the photoelectric detector does not detect the reflected signal reflected by the light reflection block, whether to control the patient table to move in the vertical direction.

After the examination of the heavy patient ends, the height of the patient table is higher than the reference height. The height sensor is further disposed to avoid a colliding movement of the patient table caused by the excessively high patient table when the patient enters the gantry of the medical device, thereby further improving the comfort of the patient.

According to the height compensation system for a patient table in the embodiments of the present disclosure, that the controller determines, according to the height compensation information, whether to control the patient table to move in the vertical direction includes: controlling, by the controller when the height compensation information is greater than or equal to a pre-determined value, the patient table to move downward in the vertical direction, until the photoelectric detector detects the reflected signal reflected by the light reflection block; and maintaining, by the controller, a horizontal height of the patient table in the vertical direction when the height compensation information is less than the pre-determined value.

When it is determined, through the height sensor, that the patient table is excessively high, the patient table is automatically controlled, by using a signal change of the photoelectric detector, to be adjusted downward in the vertical direction to the reference height, thereby improving the comfort of the patient. In addition, when the height compensation information of the patient table is within a predetermined range, the patient table is kept stationary in the vertical direction, thereby avoiding frequent adjustment on the height of the patient table.

The height compensation system for a patient table of a medical device according to the embodiments of the present disclosure further includes: a motor, disposed in the base, and configured to drive the patient table to move upward or downward in the vertical direction, the height sensor including at least one Hall sensor, where the at least one Hall sensor is disposed in the motor, and a phase difference between Hall signals generated by the at least one Hall sensor is 120°.

Hall signals with a phase difference of 120° may be counted to obtain a quantity of rotations of the motor, and further, the height compensation information of the height of the patient table can be obtained by using the quantity of rotations of the motor.

In the height compensation system for a patient table according to the embodiments of the present disclosure, the light reflection block is disposed on a lower-side outer surface of an entrance of the gantry of the medical device, an upper edge of the light reflection block is aligned with an upper surface of a bracket that is in the gantry of the medical device and that is configured to support the patient table, and the photoelectric detector is configured to emit an optical signal toward the entrance of the gantry of the medical device and detect a reflected signal of the optical signal.

A specific setting form of positions of the light reflection block and the photoelectric detector is provided. The upper edge of the light reflection block is aligned with the upper surface of the bracket that is in the gantry of the medical device and that is configured to support the patient table, to ensure that the patient table can safely and smoothly enter the gantry of the medical device after automatic height compensation.

In the height compensation system for a patient table according to the embodiments of the present disclosure, the photoelectric detector is disposed on a lower-side outer surface of an entrance of the gantry of the medical device, an upper edge of the photoelectric detector is aligned with an upper surface of a bracket that is in the gantry of the medical device and that is configured to support the patient table, and the photoelectric detector is configured to emit an optical signal in a direction opposite a direction of the entrance of the gantry of the medical device and detect a reflected signal of the optical signal; and the light reflection block is disposed on the patient table side opposite to the photoelectric detector.

A specific setting form of positions of the photoelectric detector and the photoelectric detector is provided. The upper edge of the light reflection block is aligned with the upper surface of the bracket that is in the gantry of the medical device and that is configured to support the patient table, to ensure that the patient table can safely enter the gantry of the medical device after automatic height compensation.

BRIEF DESCRIPTION OF THE DRAWINGS

The accompanying drawings described herein are used to provide further understanding of the present disclosure and construct a part of the present disclosure. Exemplary embodiments of the present disclosure and descriptions thereof are used to explain the present disclosure, and do not constitute an improper limitation to the present disclosure. In the accompanying drawings.

Reference signs are as follows:

100: height compensation system for a patient table;
101: scissors-like vertical structure;
102: light reflection block;
103: photoelectric detector;
104: controller;
105: height sensor;
S: patient table;
P: patient;
B: base;
L1 to L3: positions;
H1 to H2: heights.

DETAILED DESCRIPTION

The following clearly and completely describes the technical solutions in the embodiments of the present disclosure with reference to the accompanying drawings in the embodiments of the present disclosure. Apparently, the described embodiments are merely some of the embodiments of the present disclosure rather than all of the embodiments. All other embodiments obtained by a person of ordinary skill in the art based on the embodiments of the present disclosure without creative efforts shall fall within the protection scope of the present disclosure.

Figure 1:
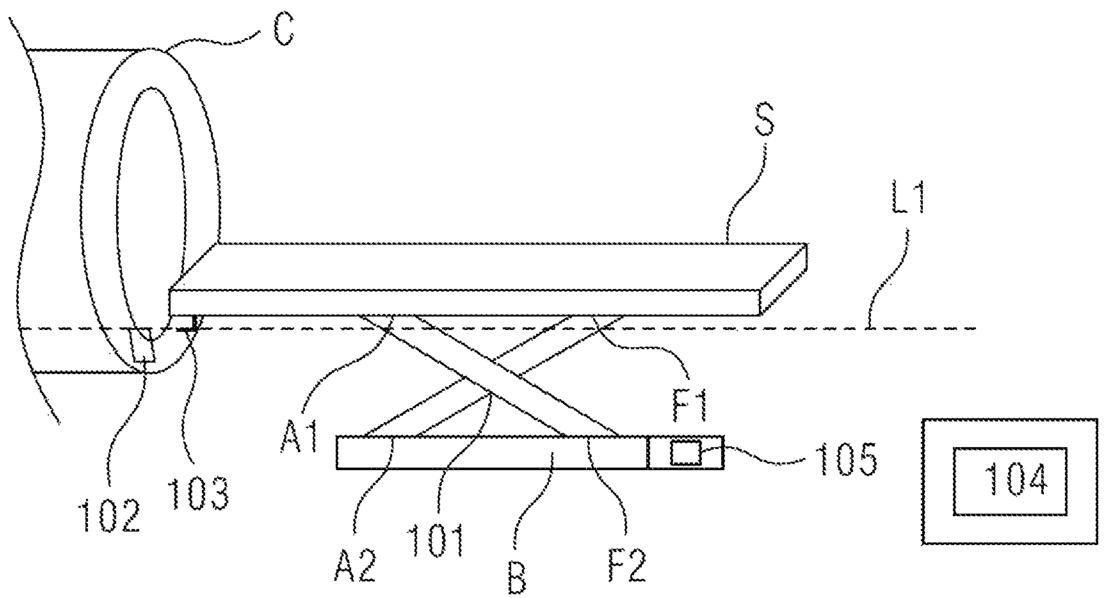
FIG. 1 is a schematic diagram of a height compensation system for a patient table according to an embodiment of the present disclosure.

The present disclosure provides a height compensation system for a patient table. FIG. 1 is a schematic diagram of a height compensation system for a patient table according to an embodiment of the present disclosure. The height compensation system for a patient table according to the embodiments of the present disclosure is described below with reference to FIG. 1.

As shown in FIG. 1, a height compensation system 100 for a patient table according to the embodiments of the present disclosure includes a scissors-like vertical structure 101, a light reflection block 102, a photoelectric detector 103, and a controller 104.

In the present disclosure, the height compensation system 100 for a patient table controls a relative position between a patient table and a gantry of a medical device. The medical device includes, but is not limited to, a medical computed tomography device (CT device), a medical MRI device, and the like.

As shown in FIG. 1, the scissors-like vertical structure 101 supports a patient table S to enable the patient table S to move in a horizontal direction and a vertical direction.

The scissors-like vertical structure 101 includes movable ends and fixed ends. The movable ends include a first movable end A1 and a second movable end A2, and the fixed ends include a first fixed end F1 and a second fixed end F2.

A first end of the patient table S, that is, a head end of the patient table S, is located at the first movable end A1 of the scissors-like vertical structure 101. A second end of the patient table S, that is, a foot end of the patient table S is located at the first fixed end F1 of the scissors-like vertical structure 101.

The first fixed end F1 is fixed to the scissors-like vertical structure 101 to support a bottom of a support plate (not shown in FIG. 1) of the patient table S. The first movable end A1 abuts against the bottom of the support plate and is movable at the bottom of the support plate. The second fixed end F2 is fixed to an end of a base B of the medical device corresponding to the second end of the patient table S. The second movable end A2 abuts against other end of the base B corresponding to the first end of the patient table S, and is movable at the other end of the base B.

In FIG. 1, C schematically represents the gantry of the medical device. When a patient enters the gantry C, the head end of the patient is located at the first end of the patient table S (that is, an end close to the gantry C), and the feet of the patient are located at the second end of the patient table S (that is, an end away from the gantry C).

For example, the light reflection block 102 is disposed on a gantry side of the medical device, for example, disposed on a lower-side outer surface of an entrance of the gantry C of the medical device. The light reflection block 102 is shown as a rectangular strip in FIG. 1. However, the present disclosure is not limited thereto. The light reflection block may be in a partial ring shape conforming to the lower-side outer surface of the entrance of the gantry C.

The light reflection block 102 may be a reflective film attached to the lower-side outer surface of the entrance of the gantry C or a block-shaped reflector made of any reflective material.

An upper edge of the light reflection block 102 is aligned with an upper surface of a bracket (not shown in FIG. 1) that is in the gantry C of the medical device and that is configured to support the patient table S. After the patient table S is sent into the gantry C in a horizontal direction, the patient table S is supported by the bracket in the gantry C.

The photoelectric detector 103 is disposed on a patient table side opposite to the light reflection block 102. For example, the photoelectric detector 103 is disposed on a lower part of the first end of the patient table S opposite to the light reflection block 102. Specifically, the photoelectric detector 103 is disposed at a bottom of the support plate on a lower part of the head end of the patient table S.

The photoelectric detector 103 is configured to emit an optical signal, such as a laser, toward the entrance of the gantry of the medical device, and can detect a reflected signal of the optical signal. When there is no patient on the patient table S, that is, when the patient table is at a reference height, the photoelectric detector 103 is located at a position L1 on the upper edge of the light reflection block 102. In this case, the optical signal emitted by the photoelectric detector 103 just cannot be reflected by the light reflection block 102.

Although FIG. 1 shows that the light reflection block 102 is disposed on the gantry side of the medical device, and the photoelectric detector 103 is disposed on the patient table side opposite to the light reflection block 102, the present disclosure is not limited thereto, and positions of the light reflection block 102 and the photoelectric detector 103 may be interchanged.

For example, the light reflection block 102 may be disposed on the patient table side, and the photoelectric detector 103 may be disposed on the gantry side of the medical device opposite to the light reflection block 102. For example, specifically, the light reflection block 102 may be disposed at the bottom of the support plate on the lower part of the head end of the patient table S, the photoelectric detector 103 may be disposed on the lower-side outer surface of the entrance of the gantry C of the medical device opposite to the light reflection block 102, and the upper edge of the photoelectric detector 103 is aligned with the upper surface of the bracket that is in the gantry of the medical device and that is configured to support the patient table S. In this case, the photoelectric detector 103 may be configured to emit an optical signal in a direction opposite a direction of the entrance of the gantry of the medical device and can detect a reflected signal of the optical signal.

The controller 104 is communicably connected to the photoelectric detector 103. For example, the controller 104 is connected to the photoelectric detector 103 in a wired or wireless manner (the wireless manner is shown in FIG. 1), receives a signal detected by the photoelectric detector from the photoelectric detector 103, and determines whether the signal detected by the photoelectric detector 103 changes.

The controller 104 can control the scissors-like vertical structure 101 to enable the patient table S to move in a vertical direction. Specifically, the controller 104 controls rotation of a motor that drives the scissors-like vertical structure 101, to control the patient table S to move upward or downward in the vertical direction.

When it is determined that the reflected signal reflected by the light reflection block 102 is detected by the photoelectric detector 103, that is, it is determined that the signal detected by the photoelectric detector 103 appears, the controller 104 sends a control signal to the motor, to control the scissors-like vertical structure 101 through the rotation of the motor to move the patient table S upward in the vertical direction, until the photoelectric detector 103 no longer detects the reflected signal reflected by the light reflection block 102, that is, the signal detected by the photoelectric detector 103 disappears. In this case, the signal detected by the photoelectric detector 103 changes according to whether the optical signal emitted by the photoelectric detector 103 is reflected by the light reflection block 102 or not.

Specifically, when the optical signal emitted by the photoelectric detector 103 is changed from not being reflected by the light reflection block 102 to being reflected by the light reflection block 102, it is determined that the signal detected by the photoelectric detector 103 changes; or the optical signal emitted by the photoelectric detector 103 is changed from being reflected by the light reflection block 102 to not being reflected by the light reflection block 102, it is determined that the signal detected by the photoelectric detector 103 changes.

In the present disclosure, the controller 103 may be a processor, a central processing unit (CPU), a computer, or the like that executes various controls and other processing according to a software program.

As shown in FIG. 1, the height compensation system for a patient table according to the embodiments of the present disclosure may further include a motor and a height sensor 105.

The height sensor 105 may include at least one Hall sensor, for example, three Hall sensors. The three Hall sensors are arranged in the motor with a phase difference of 120°. When the motor rotates, three Hall signals generated by the three Hall sensors are square wave signals with a phase difference of 120°. The three square wave signals are counted by the controller 104 to obtain a quantity of rotations of the motor. A height change corresponding to the patient table S can be determined according to a proportional relationship between the quantity of rotations of the motor and a height change of the scissors-like vertical structure 101 driven by the motor. Measuring, by using a Hall sensor disposed in a motor, a height change of a component driven by the motor is a well-known technical means in the art. To avoid too many descriptions from making the present disclosure obscure, detailed descriptions of this part are omitted.

As shown in FIG. 1, the motor is disposed at the end of the base B of the medical device corresponding to the second end of the patient table S. The height sensor 105 disposed in the motor can detect a change of a vertical height of the second end of the patient table S from the base B of the medical device relative to the reference height. That is, the change of the vertical height of the second end of the patient table S from the base B of the medical device relative to the reference height can be roughly estimated by using the three Hall sensors arranged in the motor. The reference height is a vertical height of the second end of the patient table S from the base B of the medical device when there is no patient on the patient table S, and the photoelectric detector 103 is located on the upper edge of the light reflection block 102.

The controller 104 and the height sensor 105 are communicably connected in a wired or wireless manner (the wireless manner is shown in FIG. 1). When the photoelectric detector 103 does not detect the reflected signal reflected by the light reflection block 102, the controller 104 determines, according to the change of the vertical height of the second end of the patient table S from the base B of the medical device relative to the reference height, whether to control the scissors-like vertical structure 101 to move the patient table S downward in the vertical direction.

Specifically, when the change of the vertical height of the second end of the patient table S from the base B of the medical device relative to the reference height is greater than or equal to a pre-determined value such as 3 mm, the controller 104 controls rotation of the motor to enable the scissors-like vertical structure 101 to move the patient table S downward in the vertical direction, until the photoelectric detector 103 can detect the reflected signal reflected by the light reflection block 102, that is, until the photoelectric detector 103 is exactly located on the upper edge of the light reflection block.

When the change of the vertical height of the second end of the patient table S from the base B of the medical device relative to the reference height is less than the pre-determined value such as 3 mm, the controller 104 controls rotation of the motor to keep the patient table S stationary in the vertical direction, that is, to keep a horizontal height of the patient table S in the vertical direction.

In the height compensation system for a patient table of a medical device according to the present disclosure, when a photoelectric detector detects a reflected signal reflected by a light reflection block, it is determined that a heavy patient uses the patient table, and the patient table is controlled to move upward in a vertical direction until the photoelectric detector no longer detects the reflected signal reflected by the light reflection block, thereby automatically adjusting the height of the deformed patient table upward to a reference height. When an examination of the heavy patient ends, and the height of the patient table is higher than the reference height, a height sensor is further disposed to detect height compensation information of the height of the patient table. When the patient table is excessively high, the height of the patient table is adjusted downward, thereby avoiding mechanical interference when the patient table enters the gantry of the medical device, ensuring the safety of a horizontal movement of the patient table, and improving the comfort of the patient.

Figure 2:
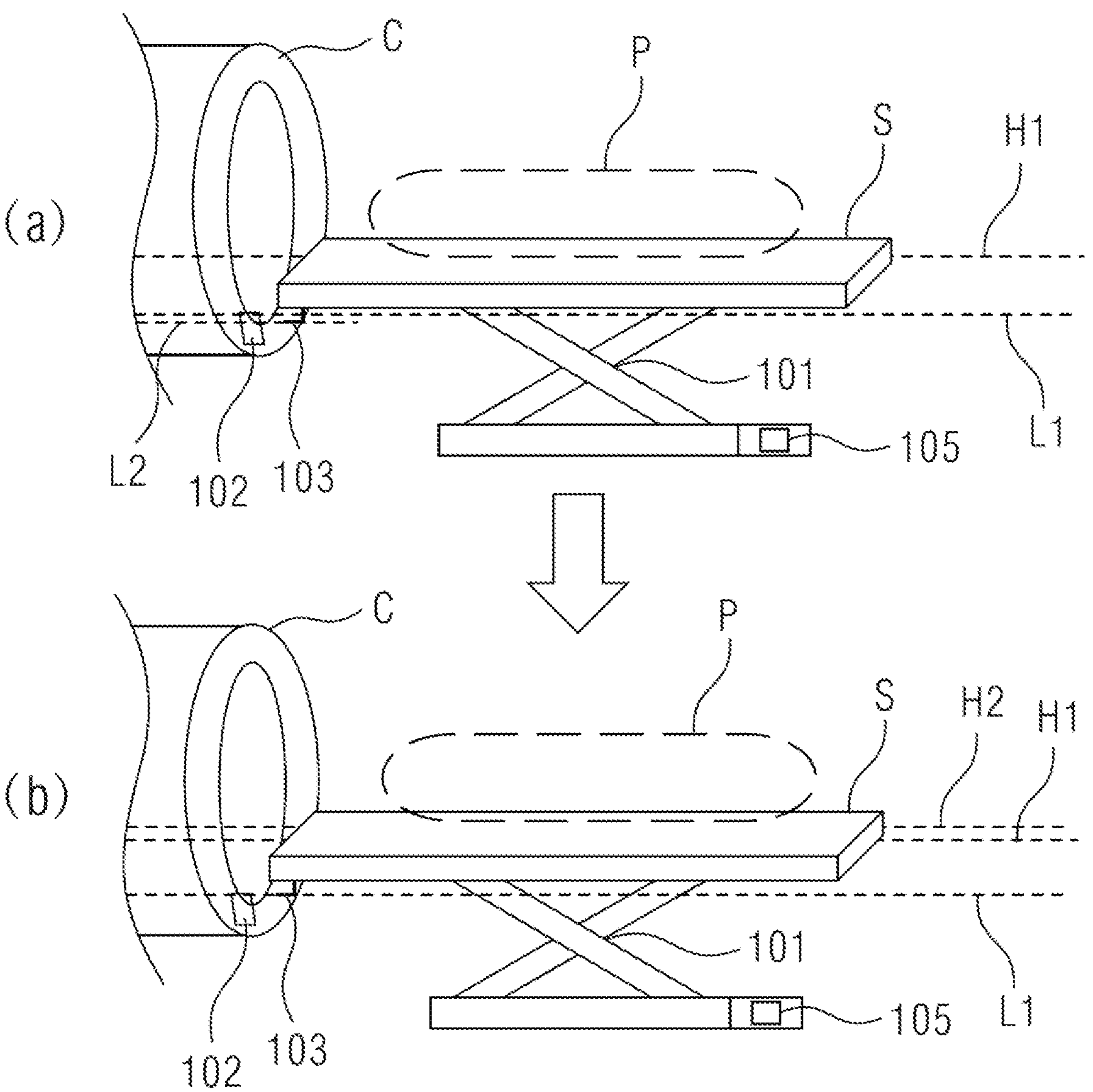
FIG. 2 is a schematic diagram of a process in which a height compensation system for a patient table performs height compensation on a patient table during an examination of a heavy patient according to the present disclosure.
Figure 3:
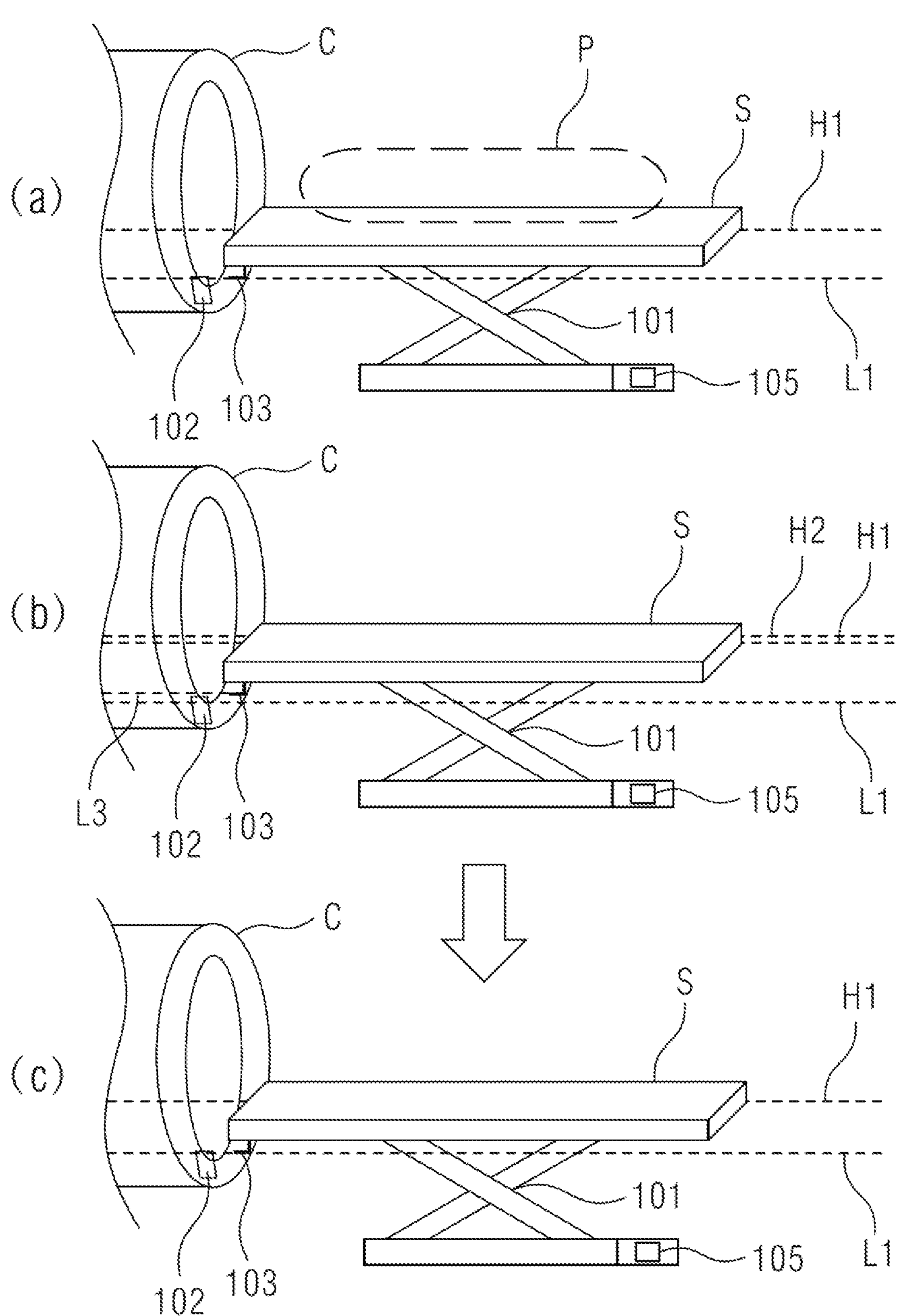
FIG. 3 is a schematic diagram of a process in which a height compensation system for a patient table performs height compensation on a patient table when an examination of a heavy patient ends according to the present disclosure.

FIG. 2 is a schematic diagram of a process in which a height compensation system for a patient table performs height compensation on a patient table during an examination of a heavy patient according to the present disclosure. FIG. 3 is a schematic diagram of a process in which a height compensation system for a patient table performs height compensation on a patient table when an examination of a heavy patient ends according to the present disclosure. For brief description, illustration of a controller 104 is omitted in FIG. 2 and FIG. 3. A height compensation method for a patient table according to the present disclosure is described in detail below with reference to FIG. 2 and FIG. 3.

As shown in (a) in FIG. 2, when a heavy patient P lies on a patient table S, a head end of the patient table S is deformed downward due to excessive pressure. Therefore, a photoelectric detector 103 located on a lower part of the head end of the patient table S descends from a position L1 on an upper edge of a light reflection block 102 to a position L2. The position L2 is located in a reflection region in which the light reflection block 102 can receive an optical signal emitted from the photoelectric detector 103 and reflect the received optical signal. In this case, a foot end of the patient table S is basically at a reference height H1 due to a relatively small deformation.

When the photoelectric detector 103 is at the position L1 on the upper edge of the light reflection block 102, the optical signal emitted by the photoelectric detector 103 just cannot be reflected by the light reflection block 102. As a result, the photoelectric detector 103 cannot receive a reflected signal reflected by the light reflection block 102. When the photoelectric detector 103 descends to the position L2 within the reflection region of the light reflection block 102, a signal emitted by the photoelectric detector 103 can be reflected by the light reflection block 102, so that the photoelectric detector 103 detects the reflected signal reflected from the light reflection block 102. That is, a signal appears and is detected by the photoelectric detector 103, and the controller 104 determines such a signal change.

As shown in (b) in FIG. 2, when an operator of the medical device, for example, a doctor, determines that the patient needs to be sent to a gantry C for examination, the controller 104 controls, according to the determined signal change detected by the photoelectric detector 103, rotation of a motor to move the patient table S upward in a vertical direction, until the photoelectric detector 103 no longer detects the reflected signal reflected by the light reflection block 102, that is, until the signal detected by the photoelectric detector 103 just disappears, and the upward movement of the patient table S is stopped. In this case, the head end of the patient table S is exactly at the position L1 on the upper edge of the light reflection block 102. Subsequently, the patient table S safely enters the gantry C and is placed on a bracket, so that a corresponding examination is performed on the patient.

As shown in (b) in FIG. 2, when the head end of the patient table S is raised to the position L1, the foot end of the patient table S also rises to a new height H2.

As shown in (a) and (b) in FIG. 3, when the heavy patient P gets out of the patient table S after the examination, the head end of the patient table S recovers from the deformation, and the height of the head end of the patient table S also returns to the height H2. In this case, the photoelectric detector 103 rises from the position L1 on the upper edge of the light reflection block 102 to a new position L3 as the head end of the patient table S recovers. In this process, the photoelectric detector 103 always cannot receive the reflected signal from the light reflection block 102. Therefore, the signal detected by the photoelectric detector 103 remains unchanged. As a result, whether a position of the patient table S is offset upward and whether height compensation on the patient table S is required cannot be determined by using the photoelectric detector 103.

In the present disclosure, the height sensor 105 provided in the motor is used to detect height compensation information H of the foot end of the patient table S rising from the reference height H1 to the height H2, to determine whether to control the scissors-like vertical structure 101 to move the patient table S downward in the vertical direction for height compensation on the patient table S.

Specifically, when the height compensation information H is greater than or equal to a pre-determined value, such as 3 mm, the controller 104 controls the scissors-like vertical structure 101 to move the patient table S downward in the vertical direction, until the photoelectric detector 103 detects the reflected signal reflected by the light reflection block 102. As shown in (c) in FIG. 3, the patient table S is lowered to the reference height H1.

When the height compensation information H is less than the pre-determined value such as 3 mm, the controller 104 controls the scissors-like vertical structure 101 to keep the patient table S stationary in the vertical direction.

In the process of performing height compensation on the patient table, when the photoelectric detector detects the reflected signal reflected by the light reflection block, it is determined that a heavy patient uses the patient table, and the patient table is controlled to move upward in the vertical direction until the photoelectric detector no longer detects the reflected signal reflected by the light reflection block, thereby automatically adjusting the height of the deformed patient table upward to the reference height. When an examination of the heavy patient ends, and the height of the patient table is higher than the reference height, a height sensor is further disposed to detect height compensation information of the height of the patient table. When the patient table is excessively high, the height of the patient table is adjusted downward, thereby avoiding mechanical interference when the patient table enters the gantry of the medical device, ensuring the safety of a horizontal movement of the patient table, and improving the comfort of the patient.

According to the embodiments of the present disclosure, a computer-readable storage medium is further provided with a program stored thereon, the program, when executed, causing the computer to execute the height compensation method for a patient table according to the embodiments of the present disclosure.

In the foregoing embodiments of the present disclosure, descriptions of the embodiments have different emphases. As for parts that are not described in detail in one embodiment, reference may be made to the relevant descriptions of the other embodiments.

The foregoing descriptions are exemplary implementations of the present disclosure. A person of ordinary skill in the art may make some improvements and modifications without departing from the principle of the present disclosure and the improvements and modifications shall fall within the protection scope of the present disclosure.

What is claimed is:

1. A height compensation system for a patient table, controlling a relative position between a patient table and a gantry of a medical device, the height compensation system comprising:

a light reflection block, which is disposed on a gantry side of the medical device or a patient table side, and is configured to reflect a received optical signal;

a photoelectric detector, which is disposed on the gantry side or the patient table side opposite to the light reflection block, and is configured to emit an optical signal outward and detect a reflected signal of the optical signal; and a controller, which is communicably connected to the photoelectric detector, and is configured to control, when the photoelectric detector detects a reflected signal reflected by the light reflection block, the patient table to move upward in a vertical direction until the photoelectric detector does not detect the reflected signal reflected by the light reflection block.

2. The height compensation system according to claim 1, wherein the light reflection block is disposed on the gantry side of the medical device, and the photoelectric detector is disposed on the patient table side opposite to the light reflection block.

3. The height compensation system according to claim 1, wherein the light reflection block is disposed on the patient table side, and the photoelectric detector is disposed on the gantry side of the medical device.

4. The height compensation system according to claim 1, further comprising:

a height sensor, which is configured to detect height compensation information of a vertical height of the patient table from a base of the medical device relative to a reference height, wherein the controller is communicably connected to the height sensor and is further configured to determine, according to the height compensation information when the photoelectric detector does not detect the reflected signal reflected by the light reflection block, whether to control the patient table to move in the vertical direction.

5. The height compensation system according to claim 4, wherein the controller determining, according to the height compensation information, whether to control the patient table to move in the vertical direction comprises:

controlling, when the height compensation information is greater than or equal to a predetermined value, the patient table to move downward in the vertical direction until the photoelectric detector detects the reflected signal reflected by the light reflection block; and maintaining a horizontal height of the patient table in the vertical direction when the height compensation information is less than the predetermined value.

6. The height compensation system according to claim 4, further comprising:

a motor, which is disposed in the base, and is configured to drive the patient table to move upward or downward in the vertical direction, wherein the height sensor comprises at least one Hall sensor disposed in the motor, and a phase difference between Hall signals generated by the at least one Hall sensor is 120°.

7. The height compensation system according to claim 1, wherein:

the light reflection block is disposed on a lower-side outer surface of an entrance of the gantry of the medical device, and an upper edge of the light reflection block is aligned with an upper surface of a bracket that is in the gantry of the medical device and that is configured to support the patient table, and the photoelectric detector is configured to emit an optical signal toward the entrance of the gantry of the medical device and detect a reflected signal of the optical signal.

8. The height compensation system according to claim 1, wherein:

the photoelectric detector is disposed on a lower-side outer surface of an entrance of the gantry of the medical device, an upper edge of the photoelectric detector is aligned with an upper surface of a bracket that is in the gantry of the medical device and that is configured to support the patient table, and the photoelectric detector is configured to emit an optical signal in a direction opposite a direction of the entrance of the gantry of the medical device and detect a reflected signal of the optical signal, and the light reflection block and the photoelectric detector are disposed on the patient table side opposite to each other.

* * * * *